United States Patent [19]

Kramer

[11] 4,046,254
[45] Sept. 6, 1977

[54] SURGICAL TRAYS

[76] Inventor: Steven G. Kramer, 355 Serrano Drive, San Francisco, Calif. 94132

[21] Appl. No.: 398,684

[22] Filed: Sept. 19, 1973

[51] Int. Cl.² ............................................. B65D 83/10
[52] U.S. Cl. .................................. 206/370; 21/56; 21/83; 21/95
[58] Field of Search ............... 206/370, 523, 524, 305, 206/306, 334, 363, 364, 365, 366, 381; 21/56, 94, 95, 83–85, 88, 89

[56] References Cited

U.S. PATENT DOCUMENTS

| | | | |
|---|---|---|---|
| 2,860,768 | 11/1958 | Smithers | 206/523 |
| 3,266,705 | 8/1966 | Wood | 206/523 X |
| 3,723,061 | 3/1973 | Stahl | 21/83 X |

FOREIGN PATENT DOCUMENTS

| | | | |
|---|---|---|---|
| 1,103,584 | 2/1968 | United Kingdom | 206/523 |

*Primary Examiner*—Stephen P. Garbe
*Attorney, Agent, or Firm*—Johnson, Dienner, Emrich, & Wagner

[57] ABSTRACT

A surgical instrument tray which may be used for protectively holding surgical instruments during sterilization and storing thereof as well as for so holding the instruments for ready accessibility thereto during an operation, the tray embodying a plurality of compartments which may be programmed as to size and location for holding complete sets of instruments therein in the order of use of the individual instruments during a particular type of surgical procedure, with the compartments embodied in resilient, sterilizable material which is effective to protect the instruments against damage.

3 Claims, 8 Drawing Figures

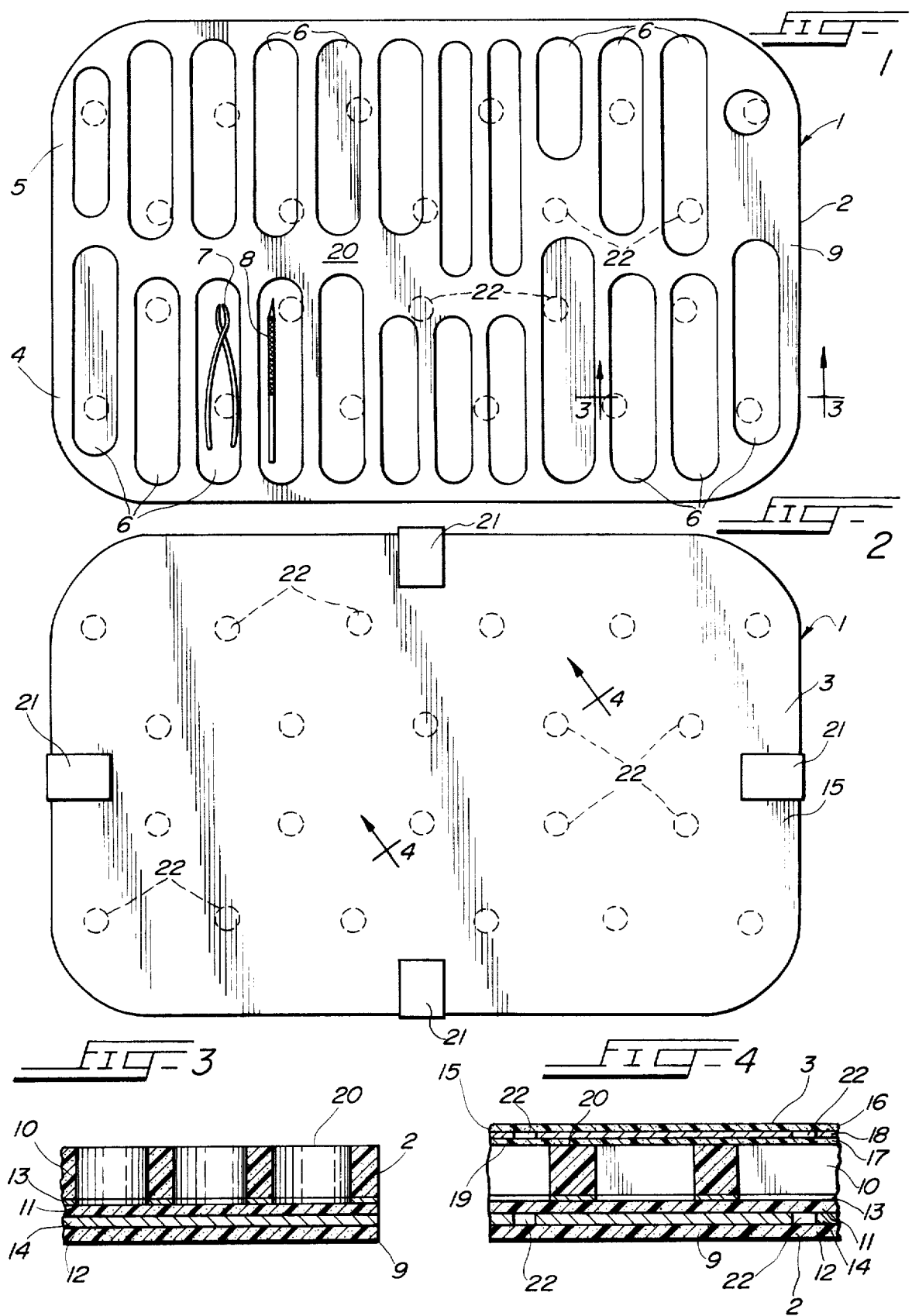

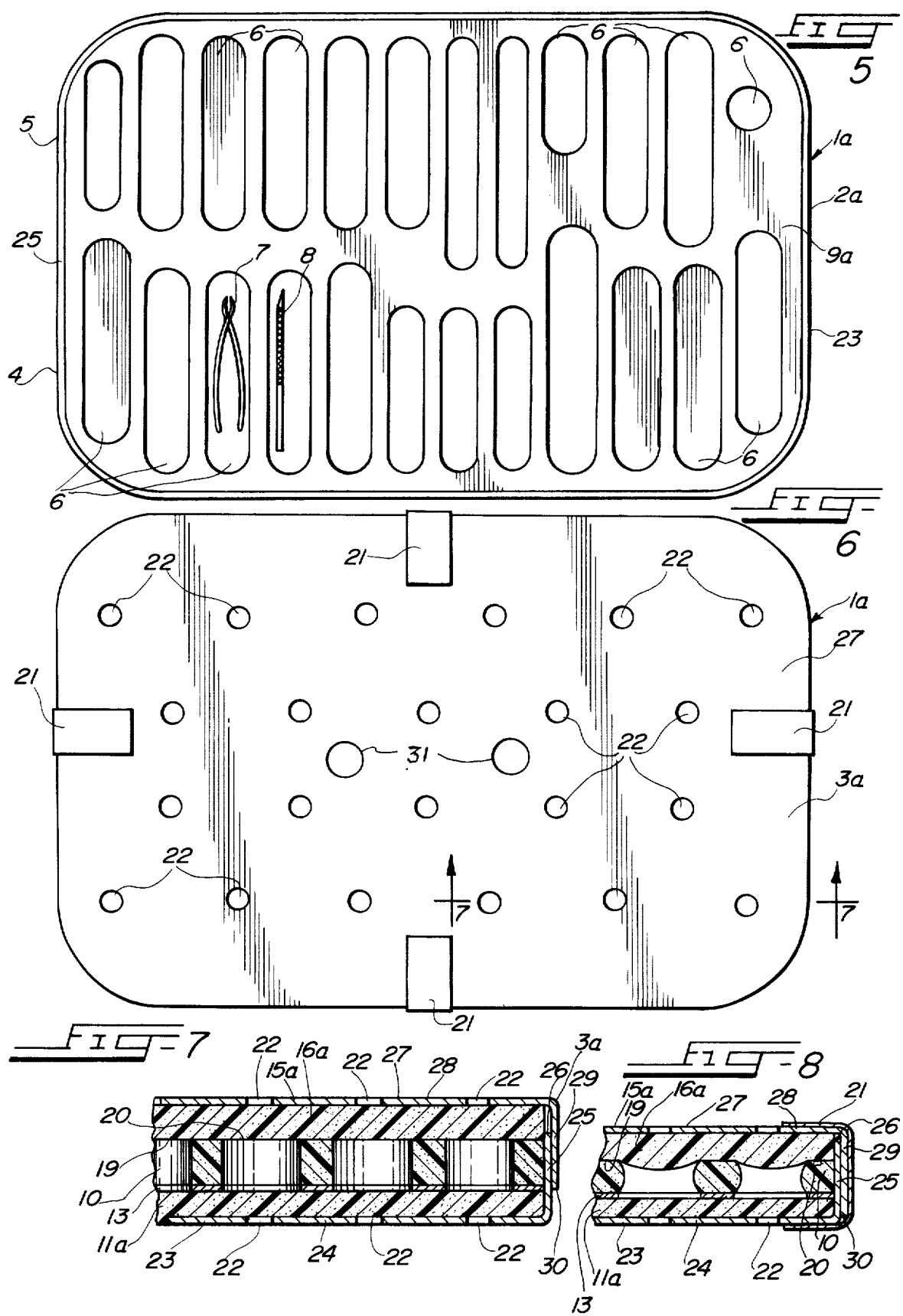

SURGICAL TRAYS

BACKGROUND OF THE INVENTION

This invention relates to surgical trays, and, more particularly, to surgical trays which are particularly well adapted for protectively holding surgical instruments.

It is a primary object of the present invention to afford a novel surgical instrument tray.

Heretofore, it has been common procedure to place surgical instruments in a metal container in the form of basins, and the like, in an operating room during an operation. Oftentimes such containers have been used during the sterilization and storing of surgical instruments, with such containers of instruments being carried to an operating room, where they are used and then returned to the containers for resterilization in preparation for the next use thereof.

Many surgical instruments are extremely delicate and very readily damaged. This is particularly true with respect to instruments used in the more delicate operations such as, for example, intraocular surgery, plastic surgery, and the like. When containers, such as metal basins, and the like are used for storing and receiving such instruments, the likelihood of accidental damage to the instruments is great, even when the instruments are handled by highly experienced personnel. It is many times greater when the personnel is not highly experienced. Such damage is commonly caused to surgical instruments handled in the aforementioned manner by reason of the instruments striking against each other or striking the metal basins, and the like. It is an important object of the present invention to protect surgical instruments from such damage in a novel and expeditious manner.

Also, heretofore, if surgical instruments used during an operation were to be prearranged in a particular order of use, it has been commonly necessary for the surgeon, or a nurse or assistant to so arrange them, such as, for example, to lay then out on a table or stand in the operating room prior to commencement of the operation. This, of course, has the disadvantage of being time consuming and requiring the services of reliable trained personnel. It has the additional disadvantage of affording an arrangement of instruments which can easily become disarranged or "scrambled" during an operation. It is another important object of the present invention to overcome such disadvantages.

Also, it is an object of the present invention to afford a novel surgical tray which is effective to overcome all such disadvantages in the storing and identification of surgical instruments, and which effectively protects such instruments from damage during sterilization, storing and transporting thereof, and even during the handling thereof in the operating room during an operation.

Surgical trays, such as, for example, trays of the type shown in Mondiadis U.S. Pat. No. 3,437,423, Kovalcik U.S. Pat. No. 3,697,223 and Stahl U.S. Pat. No. 3,723,061, for holding surgical instruments have been heretofore known in the art. However, surgical instruments trays heretofore known in the art commonly have had several inherent disadvantages such as, for example, not effectively protecting the instruments against damage; not being so constructed that the instruments therein can be readily identified other than by highly skilled personnel; not lending themselves to the effective prearrangement of instruments in a predetermined order of use; not affording any effective insurance that instruments will be returned to the proper position in the tray during and after an operation; not being readily, effectively sterilizable; being difficult to use in a operating room; or being complicated in construction and operation and difficult and expensive to produce commerically, and the like. It is another important object of the present invention to overcome such disadvantages.

A further object of the present invention is to afford a novel surgical instrument tray wherein the instruments may be disposed in individual compartments which may be so programmed as to size and location that the instruments are readily available in a predetermined order of use during an operation.

An object ancillary to the foregoing is to afford a novel surgical instrument tray wherein the parts thereof are constituted and arranged in a novel and expeditious manner such that after an instrument has been used, during an operation, it may be readily returned to its proper place in the tray so that it is easily identifiable and ready for subsequent use, if such use is called for later in the operation.

Another object of the present invention is to afford a novel surgical tray wherein the parts thereof are so constituted and arranged that the location of instruments may be diagrammed on a record card, or the like, in such a manner that the various instruments can be readily identified, even by relatively inexperienced personnel, for handing to a surgeon, as called for during an operation.

Yet another object is to afford a novel surgical instrument tray of the aforementioned type wherein the location of instruments therein may be so diagrammed on a record card, or the like, in such a manner that a count of the instruments, following an operation may be quickly and easily made; and that, by following the record card, the instruments may be readily prearranged, by inexperienced personnel, in a predetermined order in accordance with the desires of the particular surgeon who will subsequently use the instruments.

A further object of the present invention is to afford a novel surgical instrument tray which may be readily and effectively sterilized by any of the usual sterilizing processes, such as, for example, autoclaving, or gas sterilization, and the like.

Another object of the present invention is to afford a novel surgical instrument tray which affords a novel and practical carrying case for holding the instruments to be used in a particular surgical procedure, during the sterilization and storing of the instruments, and during the transporting of the sterilized instruments, from storage to the operation room, even when such transporting is from one hospital to another.

Another object of the present invention is to afford a novel surgical tray which is practical and efficient in operation, and which may be readily and economically produced commerically.

Other and further objects of the present invention will be apparent from the following description and claims and are illustrated in the accompanying drawings which, by way of illustration, show the preferred embodiments of the present invention and the principles thereof and what I now consider to be the best mode in which I have contemplated applying these principles. Other embodiments of the invention embodying the same or equivalent principles may be used and structural changes may be made as desired by those skilled in

3 the art without departing from the present invention and the purview of the appended claims.

DESCRIPTION OF THE DRAWINGS

In the drawings:

FIG. 1 is a top plan view of a surgical tray embodying the principles of the present invention, with the cover removed;

FIG. 2 is a top plan view of the surgical tray shown in FIG. 1, with the cover disposed in operative position thereon;

FIG. 3 is a fragmentary, detail sectional view taken substantially along the line 3—3 in FIG. 1;

FIG. 4 is a fragmentary, detail sectional view taken substantially along the line 4—4 in FIG. 2;

FIG. 5 is a top plan view, similar to FIG. 1, but showing a modified form of the present invention;

FIG. 6 is a view similar to FIG. 2, but showing the modified form of the present invention shown in FIG. 5;

FIG. 7 is a fragmentary, detail sectional view taken substantially along the line 7—7 in FIG. 6, but showing the cover thereof in a preliminary closed postion; and FIG. 8 is a fragmentary, detail sectional view, similar to FIG. 7, but showing the parts thereof in fully closed postion.

DESCRIPTION OF THE EMBODIMENTS SHOWN HEREIN

A surgical instrument tray 1, embodying the principles of the present invention, is illustrated in FIGS. 1-4 of the drawings to illustrate the presently preferred embodiment of the present invention.

The tray 1 embodies, in general, a base 2, FIGS. 2, 3 and 4, and a lid or cover 3, FIGS. 2 and 4, the base 1 having two rows 4 and 5 of spaced pockets or compartments 6 formed in the upper face thereof, for receiving respective individual surgical instruments therin, such as, for example, the instruments 7 and 8, shown in FIG. 1, as will be discussed in greater detail presently.

The base 2 embodies a block 9 of soft, resilient material. The block 9 is laminated in construction, embodying three layers 10, 11 and 12 of the resilient material, FIG. 3. Two supporting members or stiffeners 13 and 14 are embedded in the block 9, the supporting member 13 being disposed between the layers 10 and 11, and the supporting member 14 being disposed between the layers 11 and 12.

Similarly, the cover 3 embodies a block 15 of soft, resilient material. The block 15, also, is laminated in construction embodying two layers 16 and 17 of such material, FIG. 4. A supporting member or stiffener 18 is embedded in the block 15, being disposed between the two layers 16 and 17.

The surgical tray 1 is intended for use in holding surgical instruments during the sterilization and storage thereof, as well as during transportation of the instruments and during the use of the instruments in the operating room. As a result, it must be made of suitable material, which meets the requirments of these various uses, such as, for example, being sterilizable by the usual sterilizing processes, such as, for example, autoclaving or gas-sterilization, being lint-free, having chemical and dimensional stability under autoclaving conditions, which, normally, include temperatures of from approximately 280° to 320° F., and tending not to support growth of any microorganism, such as, for example, bacterial, fungus or viral growth, under any conditions. In addition, as will be discussed in greater detail pres-

4 ently, in the use of the tray 1, the block 9 and 15 come into an engagement with the instruments being handled therein so that the aforementioned softness and resiliency of the material from which the blocks 9 and 15 are made is of importance in protecting the surgical instruments against damage by reason of their engagement therewith.

The blocks 9 and 15 may be made of any suitable resilient material, but, preferably, are made of a sponge-like porous, resilient material having a multitude of interstices spread therethrough, such as, for example, a suitable resilient plastic material, such as foamed polyester, foamed polyurethane or foamed polyethylene. Also, the supporting members or stiffeners 13, 14 and 18, and, particularly, the stiffeners 14 and 18, preferably are relatively stiff or rigid, and may be made of any suitable material, such as, for example, chip board, cardboard, or a suitable plastic material, such as, for example, high impact polystyrene or polypropylene, or the like. The supporting member 13, primarily is embodied in the base 2 to assist in the assembling of the layers 10 and 11 in proper registration with each other, and, if desired, may be made of relatively thin, suitable material, such as polyester film. The layers 10-12 and the supporting members 13 and 14, and the layers 16 and 17 and the supporting member 18, respectively, may be secured together by any of the various suitable heat resistant adhesives which are readily available on the market.

The base 2 of the tray 1 is substantially flat, and, preferably, is substantially rectangular in cross section, with rounded corners. It may be of any suitable size, such as, for example, 11⅜ inches wide, 17⅜ inches long, and 15/16 inch thick, with the corners thereof cut on a 2 inch radius. The layers 10-12 and the supporting members 13-14, also, may be of any suitable thickness, such as, for example, the layer 10 being ⅜ inch thick, the layers 11 and 12 each being ¼ inch thick, the supporting member 13 being 0.015 inch thick and the supporting member 14 being 1/16 inch thick. The layers 10-12, and the supporting members 13 and 14, preferably, are the same size and shape, and are disposed in aligned, stacked relation to each other in the assembled base 2.

The compartments 6 are afforded by openings which extend through the layer 10 of the block 9 and the supporting member 13, the opening terminating at their lower ends at the upper face of the layer 11, FIG. 3. The openings, affording the compartments 6, may be afforded in any suitable manner, such as, for example, die-cutting the layer 10 and molding or die-cutting the supporting member 13.

In the preferred form of the tray 1 shown in the drawings, the two rows 4 and 5 of compartments 6 each embody 12 compartments, with the compartments 6 of such size, and disposed in such position as to accommodate, in the operating room, instruments for various surgical procedures, such as, for example, intraocular surgery, with the instruments being disposed in a programmed position of use starting from left to right in row 4, and continuing from left to rignt in row 5. For example, from left to right in row 4, the following instruments could be placed in the respective compartments: (1) fixation forceps; (2) tissue forceps; (3) conjunctival scissors; (4) scalpel or Beaver knife; (5) blade breaker, keratome, Ziegler, or other knife; (6) toothed conjunctival forceps; (7) plain conjunctival forceps; (8) fine corneal forceps; (9) needle holder; (10) tying forceps; (11) tying forceps; and (12) suture scissors. From left to right in row 5, the first 10 compartments 6 are adapted to receive, for example: (1) micro-scissors; (2) corneoscleral scissors (right); (3) corneoscleral scissors (left); (4) corneal scissors; (5) scleral punch; (6) capsule forceps; (7) iris retractor and lens expressor or muscle hook; (8) lens loop; (9) iris scissors; and (10) syringe with air and vitreous cannulas.

The 11th and 12th compartments in row 5 may be left empty until the tray 1 is in the operating room. Then a cautery or cyro-probe may be placed in the eleventh compartment, and an irrigation bulb, may be placed in upstanding position in the twelfth compartment, which is round in transverse cross-section.

With the tray 1 constructed in the aforementioned manner, as the surgeon finishes using a particular instrument, he can replace the instrument in the particular compartment from which it was removed, or he can hand it to a nurse or assistant for such replacement, or, if desired, he can toss the instruments onto the upper face 20 of the block 9, which, by reason of its soft, resilient nature is effective to protect such a discarded instrument from damage. At the completion of such an operation, all of the instruments may be replaced in their respective compartments 6. Thereafter, a "count" of the instruments can be made by a quick glance at the base 2 of the tray 1, it being immediately obvious if an instrument is missing from its particular compartment. After all of the instruments have thus been accounted for, the base 2, with the instruments thereon, may be appropriately cleaned, such as, for example, it may be taken to the sink and each individual instrument, with the exception of the aforementioned cautery or cyreprobe and irrigation bulb may be individually washed and then returned to its respective compartment 6. When the instruments have thus been washed and returned to the compartments 6, the tray 1 is then ready to be closed by the cover 3 and taken to the sterilization station, for sterilization and preparation for the next surgery to be performed with those instruments.

It will be remembered that the cover 3 in the preferred form of instrument tray 1 embodies the two layers 16 and 17 of the aforementioned soft, resilient material, disposed on opposite sides of a stiffener or supporting member 18. The cover 3, like the base 2, preferably is flat, and it is of the same horizontal size and shape as the base 2. In the assembled tray 1, the lower face 19 of the lower layer 17 of the block 15 rests on top of the upper face 20 of the upper layers 10 of the block 9. When the tray 1 is so assembled, the instruments in the compartments 6 thereof are confined against displacement from the respective compartments 6 in which they are disposed, and are completely surrounded by the aforementioned soft, resilient material of the blocks 9 and 15. The base 2 and the cover 3 of the thus closed tray 1 may be secured together by suitable means, such as, for example, strips of autoclaving tape 21 disposed around the junction of the outer marginal edges of the base 2 and the cover 3 in spaced relation to each other, as shown in FIG. 2, the autoclaving tape, as is well known to those skilled in the art, also serving the purpose (by its change of color) of indicating whether or not the particular tray instruments has been sterilized.

A plurality of holes 22 are formed in each of the supporting members 14 and 18, FIGS. 2 and 4, to permit the ready passage of steam, gas or other sterilant therethrough. The openings 22 may be of any suitable size and number effective to insure sterilization of the entire interior of the tray 1 during sterilization of the tray 1 and the instruments enclosed therein. It has been found that 22 openings, each having a diameter of 3/16 inch, with the openings disposed in substantially equally spaced relation to each other in the uniform pattern illustrated therefor in FIG. 2, affords sufficient passage of sterilant through the stiffeners 13, 14 and 18 to insure proper sterilization of the tray 1 and its contents. If desired, the openings 21 may extend entirely through the blocks 9 and 15. However, with the base 2 and the cover 3 constructed in the aforementioned preferred manner, wherein the blocks 9 and 15 are formed from a spongey, porous materials, such as the aforementioned polyurethane or polyethylene, the interstices therein are of such size and number that such openings are not required in the blocks 9 and 15, the sterilant readily passing therethrough.

Prior to sterilization, the tray 1, with the surgical instruments contained therein, may be placed, as a unit, in a conventional, permeable, dust-proof bag or surgical wrap in accordance with the usual practice, well known in the art. The entire unit may then be sterilized and heat dried in the usual manner, and the unit, with its surgical instrument contents, may then be stored, as a unit, at the hospital or it may be transported from one hospital to another, and is immediately ready for use in the previously described manner in the operating room during the next surgical operation. At such time, of course, the strips of tape 21, will be removed or slit so as to permit the cover 3 to be removed from the base 2 so as to expose the instruments in the compartments 6 for use.

If desired, the blocks 9 and 15 of various trays may be made of materials having different colors, to identify the particular surgical procedures for which they have been arranged, or the particular surgeons for whom they have been arranged.

In FIGS. 5–8 of the drawings, a modified form of the present invention is shown, with parts which are the same as parts shown in FIGS. 1–4 being indicated by the same reference numerals, and with parts which are similar to, but which have been substituted for parts shown in FIGS. 1–4 being indicated by the same reference numerals with suffix $a$ added thereto.

The surgical instrument tray 1a shown in FIGS. 5–8, like the surgical instrument tray 1 shown in FIGS. 1–4, embodies a base 2a and a cover 3a. In the tray 1a, the block 9a of the base 2a is disposed in an outer housing or shell 23. The shell 23 embodies a substantially flat bottom wall 24 and an upstanding sidewall 25 which projects substantially perpendicularly upwardly from the bottom wall 24 and extends around the outer periphery thereof. The block 9a, preferably, is of the same horizontal size and shape as the block 9, and the shell 23 is of such size and shape that the block 9a fits thereinto with a relatively snug, but freely slidable fit, so that, if desired, it may be quickly and easily removed and replaced.

The block 9a is of the same construction as the block 9 except that it embodies only two layers 10 and 11a of foam material, with only the one supporting member or stiffener 13 embedded therein. The layer 10 of the block 9a and the stiffener 13 of the tray 1a preferably are of the same thickness as the layer 10 and the stiffener 13 of the tray 1. The layer 11a of the block 9a, preferably, is somewhat thicker than the layer 11 of the block 9, the layer 11a, preferably, being in the nature of ⅜ of an inch thick. The depth of the interior of the shell 3 is such that when the block 9a is disposed therein in normal, at-rest position, the upper face 20 thereof is disposed a short distance, such as 1/16 inch, below the upper face 26 of the sidewall 25 of the shell 23, for a purpose which will be discussed in greater detail presently.

In the cover 3a of the tray 1a, the block 15a is disposed in a concave upwardly shell 27, which embodies a substantially flat top wall 28 with the sidewall 29 projecting downwardly from the top wall 28 in substantially perpendicular relation thereto, the sidewall 29 extending around the outer periphery of the top wall 28.

The block 15a of the tray 1a consists of only one layer 16a of the aforementioned foam material. It preferably has the same horizontal size and shape as the block 9a of the base 2a. Also, the layer 16a, preferably, is of the same construction as the layer 16, except that it is somewhat thicker, preferably being in the nature of ¼th inch thick.

The shell 27 of the cover 3a, preferably, is of such horizontal size and shape that it will fit down over the base 2a with the sidewall 29 disposed in engagement with the outer surface of the sidewall 25 with a relatively snug, but freely slidable fit. The sidewall 29 preferably is of such height, or vertical width that when the cover 3a is disposed in initial at-rest position on the base 2a, with the lower face 19 of the uncompressed block 15a resting on the upper face 20 of the uncompressed block 9a of the base 2a, the lower edge 30 of the sidewall 29 is disposed in upwardly spaced relation to the bottom wall 24 of the shell 23, as shown in FIG. 7. Thereafter, in the closing of the tray 1a, the cover 3a may be pressed downwardly into the position shown in FIG. 8, wherein the lower edge 30 of the cover shell 27 is disposed in uniplanar relation to the bottom wall 24 of the base shell 23, and the strips 21 of autoclaving tape may be secured around the marginal edges of the shells 23 and 27. In this position of the cover 3a and the base 2a relative to each other, the blocks 9a and 15a are compressed so that the instruments are closely confined in the compartments 6.

If desired, the block 15a may be adhesively secured in the shell 27 of the cover 3a. However, in the preferred type of the tray 1a, the block 15a is not secured to the shell 27. With this construction, in the assembling of the tray 1a, the block 15a may first be placed on top of the block 9a, within the upwardly projecting upper edge portion of the sidewall 25 of the shell 23. The shell 27 may then be placed in initial closing position on the shell 23, as shown in FIG. 7. In this position, the sidewall 25 of the shell 23 is free to slide upwardly between the block 9a and sidewall 29 of the shell 27 during the final closing of the tray 1a into the position shown in FIG. 8.

The shells 23 and 27 may be made of any suitable material, but preferably are made of a durable material such as stainless steel, anodized aluminum or a suitable plastic, such as, for example, high impact polystyrene or polypropylene. Like the blocks 9 and 15 of the tray 1, the shells 23 and 27 may be of selected colors, to identify the particular arrangement of instruments therein.

The bottom wall 24 of the lower shell 23, and the top wall 28 of the upper shell 27 have openings 22 extending therethrough, the opening being of the same size, and disposed in the same position on the walls 24 and 28 as that previously described with respect to the openings 22 in the supporting members 14 and 17. In addition, the top wall 28 of the tray 1a has two, centrally disposed larger openings 31, as illustrated in FIG. 6. The openings 31 afford finger-holes, through which a person may insert his thumb and middle finger, for lifting or carrying the tray 1a, and also for assisting in separating the cover 3a from the base 2a.

The manner of use of the tray 1a is the same as that heretofore described with respect to the tray 1. It will be seen that, like the tray 1, the tray 1a, affords a surgical instrument tray wherein the instruments may be stored before, during and after a surgical operation. Likewise, it affords a tray which can be sterilized, with the surgical instruments therein, by the usual sterilizing processes, such as, for example, autoclaving or gas-sterilization.

From the foregoing, it will be seen that the present invention affords a novel surgical instrument tray in which surgical instruments may be sterilized, as a unit with the tray, and thereafter stored in sterile condition therein.

Also, it will be seen that the present invention affords a novel surgical instrument tray, which affords an effective unit from which surgical instruments may be dispensed and stored during a surgical operation.

Also, it will be seen that the present invention affords a novel surgical instrument tray wherein the parts thereof are constituted and arranged in a novel and expeditious manner effective to effectively protect surgical instruments stored therein from damage.

In addition, it will be seen that the present invention affords a novel surgical instrument tray wherein surgical instruments may be disposed therein by relatively unskilled personnel, in a "programmed" manner corresponding to the order of use of a particular surgical procedure.

Also, it will be seen that the present invention affords a novel surgical instrument tray which lends itself particularly well to the diagraming of such "programming" on record cards, and the like, so that relatively unskilled personnel can readily determine which instrument is disposed in a certain compartment in the tray, which instrument may be missing from the tray, and the order in which such instruments should be placed in the tray.

Also, it will be seen that the present invention affords a novel surgical instrument tray which is practical and efficient in operation, and which may be readily and economically produced commercially.

Thus, while I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. A surgical instrument tray comprising
   a. a base having
      1. an upper face, and
      2. a plurality of spaced, upwardly opening compartments in said upper face for receiving and removably storing individual surgical instruments in respective ones of said compartments,
   b. each of said compartments having
      1. a compressible, resilient bottom wall portion, and
      2. a compressible, resilient, upstanding peripheral sidewall portion, and
   c. a cover removably mounted on top of said base,
   d. said cover having compressible, resilient portions extending across the tops of said compartments in closing relation thereto,
   e. said base including a sheet member 1. having openings therethrough corresponding to said compartments, and
2. disposed between said bottom wall portions and said sidewall portions with said openings defining the lower end portions of respective ones of said compartments.

2. A surgical instrument tray as defined in claim 1, and in which
   a. said cover includes a supporting member embedded in said last mentioned compressible resilient portions.

3. A surgical instrument tray as defined in claim 1, and in which
   a. said base includes a shell having a concavity therein,
   b. said bottom wall portion and said side wall portion are disposed in said concavity,
   c. said cover includes a shell having a concavity therein, and
   d. said compressible resilient portions of said cover are disposed in said last mentioned concavity.

* * * * *